United States Patent [19]

Arhancet et al.

[11] Patent Number: 5,648,572
[45] Date of Patent: Jul. 15, 1997

[54] COMPOSITIONS AND METHODS FOR INHIBITING VINYL AROMATIC MONOMER POLYMERIZATION

[75] Inventors: Graciela B. Arhancet, Katy; Inge K. Henrici, Spring; J. Frederick Martin, Conroe, all of Tex.

[73] Assignee: BetzDearborn Inc., Trevose, Pa.

[21] Appl. No.: 454,999

[22] Filed: May 31, 1995

[51] Int. Cl.⁶ .................. C07C 7/20; C07C 15/02; C10L 1/18; C10L 1/22
[52] U.S. Cl. .............. 585/5; 585/2; 585/3; 585/4; 585/24; 585/950
[58] Field of Search ............... 585/3, 4, 5, 2, 585/24, 950

[56] References Cited

U.S. PATENT DOCUMENTS

| | | | |
|---|---|---|---|
| 2,388,041 | 10/1945 | Craig | 202/41 |
| 4,105,506 | 8/1978 | Watson et al. | 203/9 |
| 4,389,285 | 6/1983 | Douglas et al. | 203/9 |
| 4,409,408 | 10/1983 | Miller | 585/4 |
| 4,439,278 | 3/1984 | Douglas et al. | 203/9 |
| 4,466,905 | 8/1984 | Butler et al. | 252/403 |
| 4,720,566 | 1/1988 | Martin | 558/306 |
| 4,774,374 | 9/1988 | Abruscato et al. | 585/24 |

FOREIGN PATENT DOCUMENTS

| | | |
|---|---|---|
| 163428 | 6/1976 | Czechoslovakia . |
| 0240297 | 3/1987 | European Pat. Off. . |

*Primary Examiner*—Glenn A. Caldarola
*Assistant Examiner*—Elizabeth D. Wood
*Attorney, Agent, or Firm*—Alexander D. Ricci; Philip H. Von Neida

[57] ABSTRACT

Compositions and methods for inhibiting vinyl aromatic monomer polymerization during processing are disclosed. The compositions comprise a dinitrosalicylic acid derivative and a hydroxylamine compound. The methods comprise adding the composition to the monomer during processing. The preferred composition comprises 3,5-dinitrosalicylic acid or 3,5-dinitrosalicylic methyl ester and bis-(hydroxypropyl)hydroxylamine.

12 Claims, No Drawings

COMPOSITIONS AND METHODS FOR INHIBITING VINYL AROMATIC MONOMER POLYMERIZATION

FIELD OF THE INVENTION

This invention relates to compositions and methods for inhibiting the unwanted polymerization of vinyl aromatic monomers during their processing.

BACKGROUND OF THE INVENTION

Common industrial methods for producing vinyl aromatic monomers, such as styrene, typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, although virtually excluded in styrene distillation, will also promote polymerization of the monomer.

This polymerization results not only in loss of desired end-product, but also in the loss of production efficiency caused by polymer formation and/or agglomeration of polymer on process equipment. Thermal polymerization of styrene monomer results in the formation of normal (i.e., linear) polymer. This resulting polystyrene polymer is characterized by its glassy and transparent appearance and its solubility in the styrene monomer and many organic solvents.

SUMMARY OF THE INVENTION

Methods and compositions are disclosed for inhibiting the polymerization of vinyl aromatic monomers during their processing. The present inventors have discovered that a composition comprising dinitrosalicylic acid, a derivative or isomers thereof and a hydroxylamine compound provides enhanced polymerization inhibition in vinyl aromatic monomers.

DESCRIPTION OF THE RELATED ART

Dinitrophenols and related compounds are typically in commercial use to prevent polymerization of vinyl aromatic monomers. For example, U.S. Pat. No. 4,105,506, Watson et al., teaches the use of 2,6-dinitro-p-cresol as a polymerization inhibitor of vinyl aromatic compounds. U.S. Pat. No. 4,466,905, Butler et al., teaches that 2,6-dinitro-p-cresol and p-phenylenediamine compounds will inhibit polymerization in a styrene distillation column if a minimum amount of oxygen is present. When the amount of oxygen in this column is decreased, polymerization is substantially decreased.

U.S. Pat. No. 4,389,285, Douglas et al., teaches the use of 3,5-dinitrosalicylic acid (DNSA) as a process inhibitor during the preparation of readily polymerizable ethylenically unsaturated aromatic compounds. This reference teaches that DNSA alone will act as a process inhibitor but fails to teach that other dinitrosalicylic acid derivatives or combinations with hydroxylamine compounds will inhibit polymerization in vinyl aromatic monomers. U.S. Pat. No. 4,439,278, Douglas et al., teaches the use of lower alkyl esters of 3,5-dinitrosalicylic acid as process inhibitors during the preparation of readily polymerizable ethylenically unsaturated aromatics.

U.S. Pat. No. 4,774,374, Abruscato et al., teaches compositions and processes for inhibiting the polymerization of a vinyl aromatic compound employing an oxygenated species formed by the reaction of oxygen and an N-aryl-N'-alkyl-p-phenylenediamine. U.S. Pat. No. 4,720,566, Martin, teaches methods and compositions for inhibiting polymerization of acrylonitrile in the quench tower, no oxygen excluded, using a hydroxylamine compound and a p-phenylenediamine compound.

Czechoslovakia Patent No. 163,428 teaches a method for stabilizing styrene and divinylbenzene using 2,4-dinitroorthocresol and diethylhydroxylamine. European Patent Application 0 240297 also teaches the use of this combination to inhibit polymerization of styrene. Both these disclosures treat systems at lower temperatures and higher oxygen contents. The use of diethylhydroxylamine is problematic in styrene purification processes as it has a boiling point (125° to 130° C. at 760 mm Hg) similar to that of styrene and can carry over with the styrene during purification processing.

A variety of inhibitor compositions have been employed in styrene and other vinyl aromatic monomers to inhibit undesirable polymerization. Amongst others, agents that have been used include sulfur, p-benzoquinone, phenylenediamine, tert-butyl pyrocatechol, phenothiazine, hydroxylamines, nitro compounds, and hindered phenols. However, many of these compounds present disadvantages such as high toxicity, instability and explosion hazard under elevated temperatures, or insufficient efficacy under processing conditions (i.e., inhibitor requires oxygen to be effective). The present inventors have discovered a novel composition and method for inhibiting vinyl aromatic monomer polymerization that avoids these problems associated with known inhibitors.

DETAILED DESCRIPTION OF THE INVENTION

The present invention provides for compositions and methods for inhibiting the polymerization of vinyl aromatic monomers in a processing system comprising adding to the monomers a polymerization inhibiting amount of dinitrosalicylic acid, derivative thereof or an isomer thereof and a hydroxylamine compound.

The compositions of the present invention prove efficacious at inhibiting the polymerization of vinyl aromatic monomers, particularly styrene, during their processing under monomer processing conditions. These processing conditions include but are not limited to purification and distillation of vinyl aromatic monomers.

The compositions of the present invention are effective at inhibiting the polymerization of vinyl aromatic monomers during processing conditions where oxygen is present and during oxygen-free processing conditions. The phrase "oxygen-free processing conditions" is meant to define the substantially oxygen-free conditions under which vinyl aromatic monomers, particularly styrene, are processed. These conditions which are exemplified by distillation and purification processes generally have less than two parts per million parts oxygen present and preferably less than one part of oxygen per million parts monomer present. This is in contrast to pure styrene saturated with air at room temperature which contains about sixty parts per million of dissolved oxygen.

The dinitrosalicylic acid, derivatives and isomers generally have the structure:

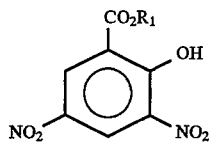

wherein $R_1$ is H, phenyl, methyl, ethyl, n-propyl, isopropyl, n-butyl and isobutyl.

Preferred dinitrosalicylic acid derivatives include but are not limited to 3,5-dinitrosalicylic acid (NS) and 3,5-dinitrosalicylic methyl ester (NSME).

The dinitrosalicylic acid isomers comprise 3,5-dinitro-4-hydroxy-benzoic acid and esters thereof wherein $R_1$ in the above formula has the same designations.

The hydroxylamine compounds useful in this invention generally have the formula:

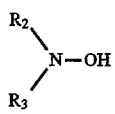

wherein $R_2$ and $R_3$ are the same or different and are hydrogen, alkyl, aryl, alkaryl, aralkyl, or hydroxyalkyl groups and preferably have about three to about twenty carbon atoms, except when $R_2$ is hydrogen, the $R_3$ is $C_6$ alkyl to $C_{20}$ alkyl. The preferred hydroxylamine compound is bis-(hydroxypropyl)hydroxylamine (HPHA).

The compositions of the present invention prove effective at inhibiting the polymerization of vinyl aromatic monomers during processing. The inventive methods provide enhanced activity or synergistic activity over either separate component at inhibiting polymerization of vinyl aromatic monomer undergoing distillation and purification processes at elevated temperatures. Styrene, for example, is typically processed at temperatures between 95° and 125° C. The methods of the present invention provide particular efficacy in high temperature (i.e., >110° C.) styrene monomer processing system.

The composition of dinitrosalicylic acid, derivative or isomer thereof and hydroxylamine compound has a weight ratio ranging from 1:9 to 9:1 with a weight ratio of 1:2 preferred.

The total amount of dinitrosalicylic acid, derivative and hydroxylamine compound used in the methods of the present invention is that amount which is sufficient to inhibit polymerization and will vary according to the conditions under which the vinyl aromatic monomer is being processed and exposed to high temperatures. At higher temperatures and higher monomer contamination, larger amounts of the polymerization inhibiting composition are required.

Preferably, the total amount of polymerization inhibiting composition added to the vinyl aromatic monomer ranges from 1 to about 10,000 parts per million parts of monomer. More preferably, the range is from about 100 parts to about 5,000 parts of the composition per million parts of monomer.

The composition can be added to the vinyl aromatic monomer by any conventional method, either as individual ingredients or as a combination of ingredients.

The composition of the present invention may be added to the vinyl aromatic monomer as either a dispersion or as a solution using a suitable liquid carrier or solvent. Any solvent that is compatible with the individual ingredients of the composition and the vinyl aromatic monomer may be employed.

Accordingly, it is possible therefore to produce a more effective vinyl aromatic monomer polymerization inhibition treatment than is obtainable by the use of either ingredient alone when measured at comparable treatment levels. This enhanced activity, particularly at temperatures of 110° C. or higher, allows for the concentration of both ingredients to be lowered and the total quantity of polymerization inhibitor required, particularly at higher processing temperatures, to be reduced.

This invention will now be further described with reference to a number of specific examples which are to be regarded solely as illustrative and not as restricting the scope of the invention.

EXAMPLES

In order to evaluate the improved polymerization inhibition of the inventive composition and to demonstrate the enhanced activity of the composition, polymerization testing was performed.

Uninhibited styrene (5.0 mL) was placed in a test tube and the designated amount of treatment was added. The tube was capped with a septum and argon was bubbled through the liquid styrene at 15 mL/min for 3 minutes. The tube was then placed in an oil bath heated to 120° C. for 2 hours. The amount of polystyrene formed was determined by methanol precipitation. Results of this testing appear in Table I.

TABLE I

| Treatment | Dosage (ppm) | % Polymer formed |
| --- | --- | --- |
| Blank | — | 7.96 |
| NSME | 300 | 1.37 |
| NSME | 600 | 0.98 |
| HPHA | 300 | 3.45 |
| HPHA | 600 | 1.49 |
| NSME/HPHA | 300/300 | 0.17 |
| | 480/120 | 0.23 |
| | 360/240 | 0.13 |
| | 240/360 | 0.17 |
| | 120/480 | 0.10 |
| | 100/500 | 0.08 |
| Blank | — | 4.62* |
| NS | 50 | 0.44* |
| NS/HPHA | 50/50 | 0.31* |

*Styrene temperature was 100° C.
NSME is 3,5-dinitrosalicylic acid methyl ester
NS is 3,5-dinitrosalicylic acid
HPHA is bis-(hydroxypropyl)hydroxylamine.

The results of this testing demonstrate that compositions of the dinitrosalicylic acid or derivative and hydroxylamine compound provide enhanced polymerization inhibiting activity in styrene monomer over that of either ingredient individually. As disclosed in U.S. Pat. No. 4,389,285,3,5-dinitrosalicylic acid (NS) inhibits the polymerization of styrene. Here the inventive composition provides enhanced activity when compared to the NS alone.

Freshly distilled uninhibited styrene (100 mL) was placed in a three-necked flask fitted with a condenser, a bubbler, and a rubber septum. The inhibitor treatment was added and argon was bubbled through the liquid at 15 mL/min with stirring from a magnetic stirrer. After 20 minutes the flask was immersed in a heated oil-bath. Argon bubbling was continued throughout the test. Samples were taken every half-hour. The amount of polystyrene formed was determined by methanol precipitation. Results of this testing are presented in Table II.

TABLE II

Styrene Polymerization Test
Distilled, uninhibited styrene at 120° C.
Treatment: 3,5-dinitrosalicylic acid methyl ester/bis-(hydroxypropyl) hydroxylamine (300/300 ppm)

| Time (min.) | % Polymer formed |
| --- | --- |
| 30 | 0.09 |
| 60 | 0.26 |
| 90 | 0.57 |
| 120 | 0.91 |
| 150 | 1.32 |
| 169 | 1.78 |

The results of this testing demonstrate that the inventive composition is effective at inhibiting the polymerization of styrene in an oxygen-free system and at elevated processing temperatures.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A composition comprising a dinitrosalicyclic acid, derivative or isomer having the structure:

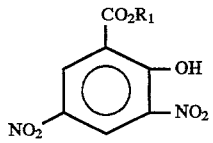

wherein $R_1$ is H, phenyl, methyl, ethyl, n-propyl, isopropyl, n-butyl and isobutyl and a hydroxylamine compound.

2. The composition as claimed in claim 1 wherein said dinitrosalicylic acid derivative is selected from the group consisting of 3,5-di-nitrosalicylic acid and 3,5-dinitrosalicylic methyl ester.

3. The composition as claimed in claim 1 wherein the hydroxylamine compound has the formula:

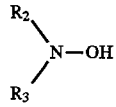

wherein $R_2$ and $R_3$ are the same or different and are hydrogen, alkyl, aryl, alkaryl, aralkyl, or hydroxyalkyl and have three to about twenty carbon atoms.

4. The composition as claimed in claim 3 wherein said hydroxylamine compound is bis-(hydroxypropyl) hydroxylamine.

5. The composition as claimed in claim 1 wherein said dinitrosalicylic acid derivative and said hydroxylamine compound are in a weight ratio of from about 1:9 to about 9:1.

6. A method for inhibiting the polymerization of vinyl aromatic monomers in a vinyl aromatic monomer processing system comprising adding to said monomers an effective polymerization inhibiting amount of a composition comprising a dinitrosalicyclic acid, derivative or isomer having the structure:

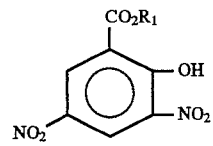

wherein $R_1$ is H, phenyl, methyl, ethyl, n-propyl, isopropyl, n-butyl and isobutyl and a hydroxylamine.

7. The method as claimed in claim 6 wherein said dinitrosalicylic acid derivative is selected from the group consisting of 3,5-dinitrosalicylic acid and 3,5-dinitrosalicylicmethyl ester.

8. The method as claimed in claim 6 wherein said hydroxylamine compound has the formula:

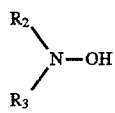

wherein $R_2$ and $R_3$ are the same or different and are hydrogen, alkyl, aryl, alkaryl, aralkyl, or hydroxyalkyl and have three to about twenty carbon atoms.

9. The method as claimed in claim 8 wherein said hydroxylamine compound is bis-(hydroxypropyl) hydroxylamine.

10. The method as claimed in claim 6 wherein said composition is added to said vinyl aromatic monomer in an amount ranging from 1 to about 10,000 parts per million parts monomer.

11. The method as claimed in claim 6 wherein said vinyl aromatic monomer has a temperature of 110° C. or higher.

12. The method as claimed in claim 6 wherein said vinyl aromatic monomer is styrene.

* * * * *